(12) United States Patent
Boyle et al.

(10) Patent No.: US 10,675,437 B2
(45) Date of Patent: Jun. 9, 2020

(54) CATHETER WITH A ROTATION CAPABILITY

(71) Applicant: The Regents of the University of California, Oakland, CA (US)

(72) Inventors: Andrew Boyle, San Francisco, CA (US); David Majure, Washington, DC (US); Randall J. Lee, Hillsborough, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/773,261

(22) PCT Filed: Mar. 10, 2014

(86) PCT No.: PCT/US2014/022664
§ 371 (c)(1),
(2) Date: Sep. 4, 2015

(87) PCT Pub. No.: WO2014/164515
PCT Pub. Date: Oct. 9, 2014

(65) Prior Publication Data
US 2016/0008571 A1 Jan. 14, 2016

Related U.S. Application Data

(60) Provisional application No. 61/780,388, filed on Mar. 13, 2013.

(51) Int. Cl.
*A61M 25/00* (2006.01)
*A61M 25/01* (2006.01)
*A61M 39/10* (2006.01)

(52) U.S. Cl.
CPC ........ *A61M 25/0026* (2013.01); *A61M 25/00* (2013.01); *A61M 25/01* (2013.01);
(Continued)

(58) Field of Classification Search
CPC .......... A61M 25/0054; A61M 25/0053; A61M 2025/0004; A61M 2025/0175;
(Continued)

(56) References Cited

U.S. PATENT DOCUMENTS

| | | | | |
|---|---|---|---|---|
| 5,352,197 A | * | 10/1994 | Hammersmark | A61M 25/01 600/585 |
| 5,391,152 A | * | 2/1995 | Patterson | A61M 25/0097 604/165.04 |
| 5,419,764 A | * | 5/1995 | Roll | A61M 25/0136 604/174 |
| 6,413,234 B1 | | 7/2002 | Thompson et al. | |
| 7,172,587 B2 | | 2/2007 | Poole et al. | |
| 7,494,478 B2 | | 2/2009 | Itou et al. | |

(Continued)

FOREIGN PATENT DOCUMENTS

JP    WO 2012114629 A1 * 8/2012 ............ A61M 25/00

*Primary Examiner* — Kevin C Sirmons
*Assistant Examiner* — Alexandra Lalonde
(74) *Attorney, Agent, or Firm* — Rudy J. Ng; Bozicevic, Field & Francis LLP (57) ABSTRACT

Aspects of the present disclosure include a catheter, such as an endovascular catheter configured for catheter rotation during a catheterization procedure, e.g., an endovascular catheterization procedure. The catheter includes a first tubular member and a second tubular member surrounding at least a portion of the central portion of the first tubular member, where the first and second tubular members are rotatable with respect to each other. Methods for performing a catheterization and kits that include the catheter are also provided.

24 Claims, 3 Drawing Sheets (52) U.S. Cl.
CPC ..... *A61M 25/0041* (2013.01); *A61M 25/0097* (2013.01); *A61M 39/10* (2013.01); *A61M 2025/0004* (2013.01); *A61M 2025/0175* (2013.01); *A61M 2039/1033* (2013.01)

(58) Field of Classification Search
CPC .............. A61M 25/0041; A61M 25/01; A61M 25/0152; A61M 25/0026; A61M 25/002; A61M 25/0029; A61M 2039/1033; A61M 2025/0681; A61M 25/0028; A61M 2025/0006; A61M 2025/0034; A61M 39/10; A61M 25/00; A61M 25/0021; A61M 25/0105; A61M 25/013; A61M 25/0113; A61M 39/1011; A61M 2039/1038; A61M 2025/09116; A61M 25/0043; A61M 2025/0059
See application file for complete search history.

(56) References Cited

U.S. PATENT DOCUMENTS

| | | |
|---|---|---|
| 7,569,046 B2 | 8/2009 | Zhou |
| 8,172,831 B2 | 5/2012 | Webler, Jr. |
| 8,784,379 B2 | 7/2014 | Akitomo |
| 2009/0149857 A1* | 6/2009 | Culbert ................. A61B 1/018 606/80 |
| 2010/0010476 A1* | 1/2010 | Galdonik ............ A61B 17/221 604/529 |
| 2011/0060264 A1* | 3/2011 | Porter .................... A61B 17/11 604/8 |
| 2011/0092910 A1* | 4/2011 | Schultz .............. A61B 17/3415 604/165.04 |
| 2011/0160739 A1* | 6/2011 | Amos ................ A61M 25/0662 606/108 |
| 2012/0184803 A1* | 7/2012 | Simon ................... A61M 1/125 600/16 |
| 2013/0197482 A1* | 8/2013 | Akitomo ............... A61M 25/00 604/527 |

* cited by examiner

CATHETER WITH A ROTATION CAPABILITY

CROSS-REFERENCE TO RELATED APPLICATION

Pursuant to 35 U.S.C. § 119(e), this application claims priority to the filing date of U.S. Provisional Application No. 61/780,388, filed Mar. 13, 2013, the disclosure of which is incorporated herein by reference.

INTRODUCTION

Percutaneous interventions to access organs within the body are commonly performed by entering through the skin, for example into the vascular system with catheters. For example, Cardiac catheters typically enter the vascular system either through a trans-radial artery approach, a trans-brachial artery approach, or a trans-femoral artery approach. Each route typically includes tortuous and/or spasmodic arterial regions that need to be navigated by the catheter en route to the heart. In addition to normal and expected tortuous and/or spasmodic regions of the arterial path, patients also commonly have idiosyncratic variations in their vascular anatomy that may present navigational challenges. Routes to other catheterization sites in the body, such as a body cavity or a hollow viscus, may present similar navigational challenges.

SUMMARY

Aspects of the present disclosure include a catheter, such as an endovascular catheter configured for catheter rotation during a catheterization procedure, e.g., an endovascular catheterization procedure. The catheter includes a first tubular member and a second tubular member surrounding at least a portion of the central portion of the first tubular member, where the first and second tubular members are rotatable with respect to each other. Methods for performing a catheterization and kits that include the catheter are also provided.

Embodiments of the present disclosure include a catheter that includes a first tubular member having a proximal portion with a proximal end, a central portion, a distal portion with a distal end, and a longitudinal axis, and a second tubular member surrounding at least a portion of the central portion of the first tubular member, the second tubular member having a proximal end, a distal end, and a longitudinal axis, where the first and second tubular members are rotatable with respect to each other.

In some embodiments, the first and second tubular members are in a fixed longitudinal relationship.

In some embodiments, the distal portion of the first tubular member extends distally beyond the distal end of the second tubular member.

In some embodiments, the first tubular member includes a lumen that extends from the proximal end to the distal end.

In some embodiments, the catheter is an endovascular catheter sized for an endovascular catheterization procedure.

In some embodiments, the catheter is configured for catheterization of a body cavity or hollow viscus of a subject.

In some embodiments, the first tubular member is configured to be rotatably drivable from the proximal end, and the second tubular member is rotationally uncoupled from the first tubular member. In some embodiments, the proximal end of the first tubular member includes one or more laterally extending tabs.

In some embodiments, the catheter includes an external surface composed of an external surface of the proximal and distal portions of the first tubular member, and an external surface of the second tubular member.

In some embodiments, the proximal and distal portions of the first tubular member have an outside diameter substantially the same as an outside diameter of the second tubular member. In some embodiments, the central portion of the first tubular member has an outside diameter less than the outside diameter of the proximal and distal portions of the first tubular member.

In some embodiments, the central portion of the first tubular member includes an external surface and the second tubular member includes a lumen having an internal surface, and the catheter further includes a lubricant between the external surface of the central portion of the first tubular member and the internal surface of the second tubular member.

In some embodiments, the catheter also includes a locking connector configured to lock the first and second tubular members into a fixed rotational relationship. In some embodiments, the locking connector is positioned at a junction between the proximal end of the second tubular member and the proximal portion of the first tubular member. In some embodiments, the locking connector is annular and includes an internal threading complimentary to a threading disposed circumferentially on an external surface of the first tubular member.

Embodiments of the present disclosure include a method of performing a catheterization. The method includes inserting the distal end of a catheter as described herein into a blood vessel, body cavity or hollow viscus of a subject, advancing the distal end of the catheter through the blood vessel, body cavity or hollow viscus, transiently occupying a tortuous and/or spasmodic region of the blood vessel, body cavity or hollow viscus with at least a portion of the second tubular member of the catheter, and rotating the proximal end of the first tubular member within the second tubular member.

In some embodiments, transiently occupying the tortuous and/or spasmodic region of the blood vessel, body cavity or hollow viscus applies frictional and/or topological constraints substantially preventing rotation of the second tubular member.

In some embodiments, the blood vessel includes a radial artery, a brachial artery, or a femoral artery.

In some embodiments, rotating the first tubular member further includes advancing the catheter through the tortuous and/or spasmodic region.

In some embodiments, the catheter includes a locking connector, and the method also includes locking the locking connector to provide the first and second tubular members in a fixed rotational relationship, and unlocking the locking connector to allow the first tubular member to rotate within the second tubular member.

Embodiments of the present disclosure include a catheterization kit that includes a sterile packaging containing a catheter. The catheter includes a first tubular member having a proximal portion with a proximal end, a central portion, a distal portion having a distal end, and a longitudinal axis, and a second tubular member surrounding at least a portion of the central portion of the first tubular member, the second tubular member having a proximal end, a distal end, and a longitudinal axis, where the first and second tubular members are rotatable with respect to each other.

Before the present invention is described in greater detail, it is to be understood that this invention is not limited to the particular embodiments described, and as such may, of course, vary. It is also to be understood that the terminology used herein is for the purpose of describing particular embodiments only, and is not intended to be limiting, since the scope of the present invention is embodied by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, it will be readily apparent to one of ordinary skill in the art in light of the teachings herein that certain changes and modifications may be made thereto without departing from the spirit and scope of the appended claims. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. To the extent such publications may set out definitions of a term that conflicts with the explicit or implicit definition of the present disclosure, the definition of the present disclosure controls. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

DETAILED DESCRIPTION

Aspects of the present disclosure include a catheter, such as an endovascular catheter configured for catheter rotation during a catheterization procedure, e.g., an endovascular catheterization procedure. The catheter includes a first tubular member and a second tubular member surrounding at least a portion of the central portion of the first tubular member, where the first and second tubular members are rotatable with respect to each other.

In some instances, both normal and anomalous tortuous and/or spasmodic regions of the vascular system can complicate percutaneous catheterization procedures by increasing friction against the catheter and the vessel wall and/or decreasing the maneuverability of the catheter. Examples of embodiments of catheters and methods of using them, as provided herein, include endovascular catheters directed toward cardiac procedures, however, the full scope of embodiments of the provided technology includes catheters and their application to targets anywhere within the vascular space. Accordingly, tortuosity or spasm within an arterial conduit to the heart can complicate catheterization procedures, such as cardiac procedures. Rotating the catheter is one way to maneuver the leading distal end of the catheter through a complex path as the catheter is advanced toward a target site.

As described herein, catheters of the present disclosure may be described, for example, in relation to a catheterization procedure, such as an endovascular catheterization using a catheter configured for an endovascular catheterization. These descriptions herein are examples of embodiments of the present disclosure, and the full scope of embodiments of the present disclosure includes catheters and catheterization methods directed to a blood vessel (e.g., artery or vein), a body cavity (e.g., abdominal, thoracic, pelvic, pericardial space, etc.), and a hollow viscus (e.g., bladder, stomach, intestines, etc.), and the like, of a subject.

In some cases, the rotatability of conventional catheters can be hindered by surface-to-surface (e.g., the arterial wall and catheter surfaces) frictional resistance to rotation associated with passing through a complex vascular route or lumen. Additionally, rotation of a typical catheter may be hindered by acute angles within the vasculature or lumen, causing bending or impingement of the catheter. In effect, a conventional catheter can become rotationally trapped or stilled by a tortuous arterial route or lumen. In some instances, blood vessels can spasm, which may increase the friction against the catheter and may rotationally trap the catheter as described above. Rotatability can also be resisted by factors such as topological constraints with regard to the arterial path, spasm of the artery on the catheter, or by the relative flexibility of the catheter. As used in the present disclosure, frictional resistance will be considered to include these related considerations as well. Embodiments of the present disclosure may facilitate a reduction in the impediment represented by this frictional resistance to rotation by preserving the rotational ability of the distal end of the catheter, while providing a non-rotating (or not-necessarily rotating) surface proximal to the distal end of the catheter.

Accordingly, embodiments of a catheter and methods of use are provided. Structural embodiments can be sized and configured to be appropriate for any vascular or lumen path conventionally used to provide access to the heart or other catheterization site in the body, such as, but not limited to, a body cavity (e.g., abdominal, thoracic, pelvic, pericardial space, etc.), a hollow viscus (e.g., bladder, stomach, intestines, etc.), and the like. Catheter embodiments of the present disclosure may be described from the perspective of (a) the structural and functional relationships between two tubular members, as well as from the perspective of (b) the structural and functional relationships among longitudinally arranged portions of the catheter. Certain embodiments of methods of using the catheter relate to rotating the catheter, such as in association with advancing the catheter through the vasculature or lumen, and navigating the distal end of the catheter toward a desired catheterization site.

Catheters

From one perspective, certain embodiments of the catheter may be understood in terms of the structural and functional relationships between two tubular members. Embodiments of a catheter may include a first tubular member and second tubular member. In certain embodiments, the first tubular member has a proximal portion with a proximal end, a central portion, a distal portion with a distal end, and a longitudinal axis. As used herein, "proximal" refers to the end of a device nearer to the operator, and "distal" refers to the end of the device further away from the operator. In some cases, the proximal end is adapted to be handled by an operator during a catheterization procedure. For instance, the proximal end of the catheter may include a gripable portion, such as a handle, and the like, and may be provided with one or more user input elements, such as, but not limited to, a button, a trigger, a dial, a lever, a tab, combinations thereof, and the like. An operator, in a typical working context, may include a physician, such as, by way of example, an interventional cardiologist.

In certain embodiments, the second tubular member includes a proximal end, a distal end and a longitudinal axis. In some instances, the second tubular member is configured to surround at least a portion of the central portion of the first tubular member. Stated another way, the second tubular member may be disposed such that the central portion of the first tubular member is nested within the second tubular member. For example, the central portion of the first member may be disposed within the second tubular member. In certain cases, the first and second tubular members are rotatable with respect to each other. Rotatability may also be understood as the catheter being rotatable with respect to an artery that the catheter has been placed within. The first and second tubular members may be freely rotatable with respect to each other.

In certain embodiments, the first and second tubular members are in a fixed longitudinal relationship. For example, the first and second tubular members may be configured such that the central portion of the first tubular member is disposed within the second tubular member, as described above, and the second tubular member does not significantly move longitudinally with respect to the first tubular member. As such, in some instances, the first and second tubular members are configured such that the second tubular member may freely rotate about the central portion of the first tubular member but does not significantly slide over the first tubular member in either a proximal or distal direction.

The present disclosure relates to catheters. For example, some embodiments of the present disclosure are directed to an endovascular catheter sized and configured for a cardiac catheterization procedure. In some instances, the procedure may include entry into an artery and advancement therethrough to a heart, the artery being any of a radial artery, a brachial artery, or a femoral artery. Embodiments of the endovascular catheter are variously sized and configured to be appropriate for each site of arterial entry and the ensuing respective arterial path to the heart. For example, in certain embodiments, the catheter has a length ranging from 5 cm to 500 cm, such as from 10 cm to 250 cm, including from 25 cm to 200 cm, or from 50 cm to 150 cm. In certain instances, the catheter has a length of 100 cm.

In certain embodiments, the proximal portion of the first tubular member has a length ranging from 1 cm to 100 cm, such as from 1 cm to 75 cm, including from 1 cm to 50 cm, or from 1 cm to 25 cm, or from 1 cm to 20 cm, or from 1 cm to 15 cm, or from 5 cm to 15 cm. In certain instances, the proximal portion of the first tubular member has a length of 10 cm. In certain embodiments, the central portion of the first tubular member has a length ranging from 10 cm to 250 cm, such as from 10 cm to 200 cm, including from 10 cm to 150 cm, or from 10 cm to 125 cm, or from 10 cm to 100 cm, or from 25 cm to 100 cm, or from 50 cm to 100 cm. In certain instances, the central portion of the first tubular member has a length of 80 cm. In certain embodiments, the distal portion of the first tubular member has a length ranging from 1 cm to 100 cm, such as from 1 cm to 75 cm, including from 1 cm to 50 cm, or from 1 cm to 25 cm, or from 1 cm to 20 cm, or from 1 cm to 15 cm, or from 5 cm to 15 cm. In certain instances, the distal portion of the first tubular member has a length of 10 cm.

In certain embodiments, second tubular member has a length substantially the same as the central portion of the first tubular member. For example, the second tubular member may have a length ranging from 10 cm to 250 cm, such as from 10 cm to 200 cm, including from 10 cm to 150 cm, or from 10 cm to 125 cm, or from 10 cm to 100 cm, or from 25 cm to 100 cm, or from 50 cm to 100 cm. In certain instances, the second tubular member has a length of 80 cm.

Other lengths for the catheter are also possible depending on the type of catheterization procedure. For instance, the catheter may be configured for arterial catheterization and may have lengths as described above. In other embodiments, the catheter may be configured for venous catheterization, and may have lengths similar to that described above. In other embodiments, the catheter may be configured to facilitate percutaneous access to a body cavity (e.g., abdominal, thoracic, pelvic, pericardial space, etc.), or a hollow viscus (e.g., bladder, stomach, intestines, etc.), and may have shorter lengths, such as a length of 100 cm or less, such as 75 cm or less, or 50 cm or less, or 25 cm or less, or 10 cm or less, or 5 cm or less. The lengths of the proximal, central and distal portions of the first tubular member and the second tubular member may also be correspondingly shorter.

In certain embodiments, the first and second tubular members of the catheter each have a distal end. In some cases, the distal portion of the first tubular member extends distally further than the distal end of the second tubular member. For instance, the distal end of the first tubular member may be the distal end of the catheter as a whole.

Further with respect to the first tubular member, certain embodiments include a continuous lumen that extends from the proximal end of the first tubular member (and the proximal end of the catheter as a whole) to the distal end of the first tubular member (and the distal end of the catheter as a whole). As described above, the proximal end of the first tubular member may be adapted to be handled by an operator during a catheterization procedure. In some instances, the proximal end of the first tubular member may include an adaption such as laterally extending tabs that can facilitate rotation of the catheter by the operator during a procedure.

Embodiments of the catheter may be configured for axial rotation. In some embodiments of the catheter, the first tubular member is rotatably drivable from the proximal end (e.g., by an operator using a rotation control mechanism). In certain instances, the second tubular member is rotationally uncoupled with respect to the proximal end of the first tubular member. Stated in another way, in certain embodiments, the second tubular member is freely rotatable around the first tubular member. In some cases, in contrast to the first tubular member whose rotation is controllable by an operator, the second tubular member may be passively rotatable with respect to the first tubular member. As such, in certain embodiments, the first tubular member may be freely rotatable within the second tubular member, where the second tubular member is held rotationally still, e.g., by frictional resistance during use, or may rotate at a different rate and/or in a different rotational direction with respect to the first tubular member. For example, by being passively rotatable, the second tubular member may be subject to external constraints, such as may be provided by a vascular wall, which can physically prevent rotation of the second tubular member.

Further rotational aspects of the second tubular member are summarized below, where a locking mechanism, when engaged, can confer a drivable rotatability. In some cases, the second tubular member is configured to be lockably engaged (e.g., rotationally coupled) to the first tubular member. As such, in embodiments where the second tubular member is coupled to the first tubular member, the second tubular member may rotate in conjunction with the rotation of the first tubular member.

Some aspects of rotation can be described in terms of external surfaces that engage the vasculature when the catheter is in use. Embodiments of the catheter as a whole have an external surface. The proximal, central, and distal portions of the first tubular member, and the second tubular member each have, respectively, an external surface. In some embodiments, the external surface of the catheter is represented by the external surfaces of the proximal and distal portions of the first tubular member, and the external surface of the second tubular member. In certain instances, the external surface of the central portion of the first tubular member is enclosed within the second tubular member, and thus is not an external surface of the catheter as a whole.

In certain embodiments, the proximal and distal portions of the first tubular member and the second tubular member each have outside diameters that are substantially the same. In some embodiments, the external surface of the central portion of the first tubular member is recessed inward with respect to the external surfaces of the proximal and distal portions of the first tubular member. This recessed aspect of the central portion of the first tubular member may be configured to accommodate the surrounding second tubular member such that the outside diameter of the catheter remains substantially the same throughout the length of the catheter. For instance, the outside diameter of the central portion of the first tubular member may be less than the outside diameter of the proximal and distal portions of the first tubular member.

As described above, in certain embodiments, the outside diameter of the catheter is substantially the same along the length of the catheter. For example, the outside diameter of the catheter may be 20 mm or less, or 19 mm or less, or 18 m or less, or 17 mm or less, or 16 mm or less, or 15 mm or less, or 14 mm or less, or 13 mm or less, or 12 mm or less, or 11 mm or less, or 10 mm or less, such as 9 mm or less, including 8 mm or less, or 7 mm or less, or 6 mm or less, or 5 mm or less, or 4 mm or less, or 3 mm or less, or 2 mm or less, or 1.5 mm or less, or 1 mm or less. In some instances, a catheter suitable for endovascular catheterization has an outside diameter of 2 mm or less. Stated another way, in certain embodiments, the outside diameter of the catheter is 34 French or less, or 32 French or less, or 30 French or less, or 28 French or less, or 26 French or less, or 24 French or less, or 22 French or less, or 20 French or less, such as 19 French or less, including 18 French or less, or 17 French or less, or 16 French or less, or 15 French or less, or 14 French or less, or 13 French or less, or 12 French or less, or 11 French or less, or 10 French or less, or 9 French or less, or 8 French or less, or 7 French or less, or 6 French or less, or 5 French or less, or 4 French or less, or 3 French or less. In some instances, a catheter suitable for endovascular catheterization has an outside diameter of 5 French or less.

Other outside diameters for the catheter are also possible depending on the type of catheterization procedure. For instance, the catheter may be configured for arterial catheterization and have an outside diameter as described above. In other embodiments, the catheter may be configured for venous catheterization, and may have an outside diameter similar to that described above. In other embodiments, the catheter may be configured to facilitate percutaneous access to a body cavity (e.g., abdominal, thoracic, pelvic, pericardial space, etc.), or a hollow viscus (e.g., bladder, stomach, intestines, etc.), and may have an outside diameter larger than the outside diameter of an endovascular catheter. For instance, a catheter configured to facilitate access to a body cavity or hollow viscus may have an outside diameter of 5 mm or more, such as 6 mm or more, or 7 mm or more, or 8 mm or more, or 9 mm or more, or 10 mm or more, or 11 mm or more, or 12 mm or more, or 13 mm or more, or 14 mm or more, or 15 mm or more, or 16 mm or more, or 17 mm or more, or 18 mm or more, or 19 mm or more, or 20 mm or more. In some instances, a catheter configured to facilitate access to a body cavity or hollow viscus may have an outside diameter of 15 French or more, such as 16 French or more, or 17 French or more, or 18 French or more, or 19 French or more, or 20 French or more, or 22 French or more, or 24 French or more, or 26 French or more, or 28 French or more, or 30 French or more, or 32 French or more, or 34 French or more.

In certain embodiments, the inside diameter of the catheter is less than the outside diameter of the catheter to accommodate the thickness of the walls of the catheter while still maintaining an interior lumen having an inside diameter sufficiently large enough to provide a working space for the operator, e.g., for the insertion of one or more medical devices through the catheter, such as, but not limited to a guidewire, and the like. In some instances, the inside diameter of the catheter is substantially the same along the length of the catheter. For example, the inside diameters of the proximal, central and distal portions of the first tubular member may be substantially the same along the length of the catheter. In certain instances, the inside diameter of the first tubular member is 9.5 mm or less, such as 9 mm or less, including 8.5 mm or less, or 8 mm or less, or 7.5 mm or less, or 7 mm or less, or 6.5 mm or less, or 6 mm or less, or 5.5 mm or less, or 5 mm or less, or 4.5 mm or less, or 4 mm or less, or 3.5 mm or less, or 3 mm or less, or 2.5 mm or less, or 2 mm or less, or 1.5 mm or less, or 0.5 mm or less. In certain cases, the inside diameter of the first tubular member is 1.5 mm or less.

Embodiments of the catheter have an external surface as a whole, extending from the proximal end to the distal end of the catheter. In some embodiments of the catheter, the first and second tubular members each have an external surface, and the external surface of the first tubular member provides the external surface of the proximal and distal portions of the catheter, and the external surface of the second tubular member provides the external surface of the central portion of the catheter. In some embodiments of the catheter, the external surfaces of the first tubular member are rotatable, as driven by the operator, whereas the surface of the second tubular member is not operably connected to the first tubular member, and thus not rotationally drivable. This aspect of the provided catheter may facilitate rotation of the first tubular member when the second tubular member is rotationally constrained or entrapped by the surrounding arterial anatomy that the catheter is transiently occupying.

Some embodiments of the catheter include a composition that facilitates the rotation of the first and second members with respect to each other. In certain instances, the first and second tubular members each have an internal or luminal surface and an external surface. In various embodiments of the catheter, the external surface of first tubular member and/or the internal surface of second tubular member may include a lubricious coating. For example, the catheter may include a lubricant disposed between the external surface of the central portion of the first tubular member and the internal surface of the second tubular member.

Aspects of the function of the first and second tubular members are described below. In certain embodiments, the first tubular member makes up the full length of the catheter, and is rotatable by the operator. In some cases, the external aspect of the first tubular member represents the external surface of the catheter as a whole in the proximal and distal portions of the catheter. In certain embodiments, the distal portion of the first tubular member (and the catheter) of the catheter includes a distal end. In some cases, the distal end of the first tubular member includes a curved distal tip that may be configured to facilitate guidance of the distal tip of the catheter into a target artery. The operator may, for example, want to guide the catheter from the large lumen of the aorta into the coronary artery. Rotation of the first tubular member, as driven by the operator, manifests as rotation of the catheter's distal tip. In certain instances, the distal tip and its rotation can facilitate controlling the navigation of the catheter as it is advanced through an artery.

In certain embodiments, the central portion of the catheter is externally represented by the second tubular member, which, as described above may be rotationally uncoupled from the first tubular member within second tubular member. This non-rotating central portion of the catheter, when located within a tortuous or spasmodic vascular region, may facilitate the rotation of the distal portion and distal tip of the first tubular member, while the external aspect of the central portion of the catheter (e.g., the second tubular member) does not rotate. In some instances, the second tubular member, in effect, provides a substantially friction-free, or friction-insulated zone within which the first tubular member can rotate with substantial freedom.

In some embodiments of the present disclosure, a locking mechanism may be provided that is configured to rotationally couple the second tubular member to the first tubular member. As such, an operator may be provided with the option to engage the central portion of the catheter (e.g., the second tubular member) such that it rotates in accordance with torque applied to the proximal end of the first tubular member. Accordingly, some embodiments may include a locking connector which, when locked, locks the first and second tubular members into a fixed rotational relationship such that rotation of the first tubular member drives rotation of the second tubular member. In certain embodiments, the locking connector is positioned at a junction between the proximal end of the second tubular member and the proximal portion of the first tubular member. For example, the locking connector may be configured to lock the first and second tubular members at the junction where the distal end of the proximal portion of the first tubular member and the proximal end of the second tubular member meet.

In effect, such a locking mechanism functions as rotation on/off control for the central portion of the catheter (e.g., the second tubular member). When the locking mechanism is engaged in a locked position, the catheter is able to perform, in a rotational sense, in a manner substantially the same as a conventional endovascular catheter performs rotationally. When the locking mechanism is not engaged, the catheter is configured to perform with the rotational capabilities as described herein. In certain embodiments, an option to assume rotational performance of a conventional catheter may be advantageous with regard to navigating or advancing the catheter through uncomplicated regions of the vasculature.

Embodiments of a locking mechanism that can rotationally couple and uncouple the first and second tubular members may include a variety of different mechanisms that serve similar functions. In one example of such a locking mechanism, the locking connector may be an annular element. In certain embodiments, the annular locking connector may be fixed externally to the second tubular member at the proximal end of the second tubular member (or may be formed from the same material as the second tubular member as a single contiguous piece). In certain cases, the annular element includes an internal threading complimentary to a threading disposed circumferentially on an external surface of the first tubular member. Other types of connections may be provided, such as, but not limited to, snap-fit connections, Luer-lock type connections, and the like.

From a second perspective, embodiments of the present disclosure may be understood in terms of the structural and functional relationships among longitudinally arranged portions of the catheter. Accordingly, some embodiments of a catheter may include three longitudinally arranged portions, a proximal portion, a central portion, and a distal portion. These catheter embodiments may further include an external surface extending the length of the catheter, across each portion of the catheter, and a continuous central lumen through the catheter.

Embodiments of the catheter include a proximal end and a distal end. In certain instances, the proximal end may be adapted to be handled by an operator during a catheterization procedure, as for example, the operator may rotate the catheter from the proximal end using a rotation control mechanism. In these embodiments, thus, the external surfaces of proximal and distal portions are rotatable as driven by the operator handling the proximal end of the catheter. In some cases, the external surface of the central portion is rotatably independent with respect to the proximal and distal portions of the catheter. Thus, in some embodiments, the central portion may not rotate (or rotate at a different rate and/or in a different rotational direction) when the external surfaces of proximal and distal portions are being driven by the rotation control mechanism.

Additional aspects of the various portions of the catheter are described below. In certain embodiments, the distal portion of the catheter may include a distal tip, such as a curved distal tip. In some instances, the distal tip is configured to facilitate advancement of the catheter without significantly traumatizing the arterial wall that the catheter may contact during use. Rotation of the proximal portion of the catheter, as driven by the operator, manifests as rotation of the catheter's distal tip. In some cases, the distal tip and its corresponding rotation may facilitate controlling the navigation of the catheter as it is advanced through an artery.

In certain embodiments, the central portion of the catheter may be rotationally uncoupled from the proximal and distal portions of the catheter, such that the central portion does not rotate (or may rotate at a different rate and/or different rotational direction) while the distal end rotates. As described above, the central portion of the catheter, when located within a tortuous or spasmodic vascular region, may facilitate rotation of the distal portion of the catheter, while the central portion does not substantially rotate, or may rotate at a different rate and/or different rotational direction. In certain embodiments, the proximal portion of the catheter may be outside the body during a cardiac catheterization procedure. In some cases, the distal portion of the catheter rotates in concert with the proximal portion, both portions being operatively connected and rotationally responsive to the rotation by the operator. For example, the proximal and distal portions of the catheter may be formed from a contiguous first tubular member having a second tubular member surrounding the central portion of the first tubular member, as described above.

In certain embodiments, the catheter may be made of a material compatible with a catheterization procedure (e.g., an endovascular catheterization procedure). In some instances, the catheter material is compatible with body tissues and/or aqueous media, e.g., the catheter material is substantially inert (non-reactive) towards tissues and/or surrounding media during use. For example, the catheter material may include, but is not limited, to a polymer (e.g., polytetrafluoroethylene (PTFE), nylon, polyurethane, etc.), a metal or alloy (e.g., nitinol, stainless steel, etc.), or combinations thereof. In some instances, the catheter may be composed of metal wire, such as a braided metal wire. The catheter may be composed of a combination of different materials, such as a combination of a polymer and a metal, e.g., a braided metal wire coated with a polymer. In certain embodiments, the various portions of the catheter may be composed of the same materials. In other embodiments, the various portions of the catheter may me composed of different materials depending on the portion of the catheter, the type of procedure being performed, the expected tortuosity of the vasculature, the incidence and/or severity of spasm, etc. For instance, the proximal portion of the catheter may be composed of a material suitable for interfacing with an operator control device, e.g., for controlling the advancement and rotation of the catheter. In certain cases, the central and/or distal portions of the catheter may be composed of a material different from the proximal portion of the catheter.

For example, the central and/or distal portions of the catheter may be composed of a material that is more flexible than the material of the proximal portion of the catheter.

Figure 1:
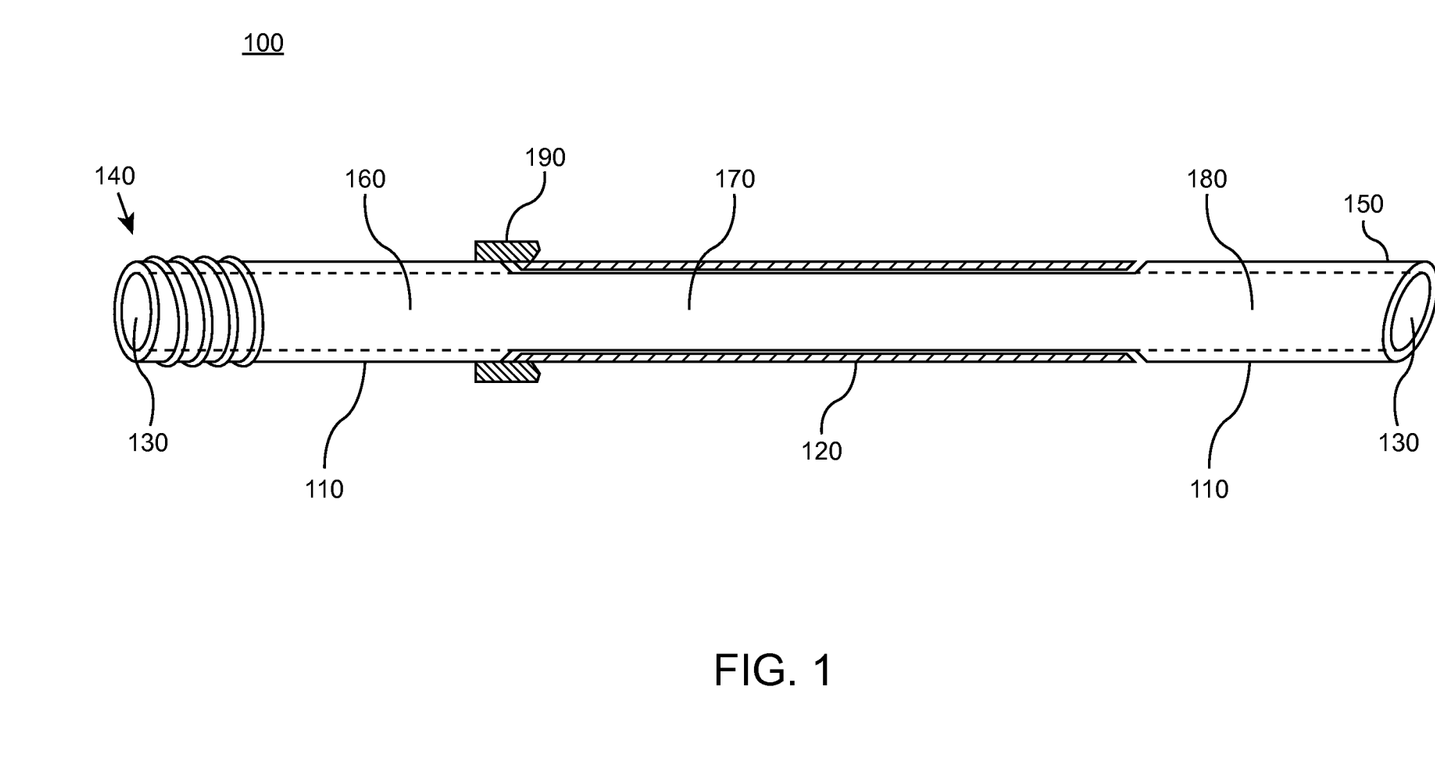
FIG. 1 shows a partial cut-away side view of an embodiment of a catheter, according to embodiments of the present disclosure.

FIG. 1 shows a partial cut-away side view of an embodiment of a catheter 100. As shown in FIG. 1, the central lumen 130 of the catheter 100 is defined by a first tubular member 110, which is continuous from the proximal end 140 to the distal end 150 of the catheter 100. The first tubular member 110 includes a proximal portion 160 and a distal portion 180, with a central portion 170 between the proximal and distal portions of the first tubular member 110. The central portion 170 of the first tubular member 110 is surrounded by (e.g., nested within) a second tubular member 120 along the length of a central portion 170 of the catheter 100. The first tubular member 110 and second tubular member 120 are disposed in a longitudinally fixed relationship. As such, the first and second tubular members may be fixed, fused, connected, or otherwise longitudinally stabilized at the proximal and/or distal ends of the second tubular member 120, such that there is substantially no longitudinal slippage between the first and second tubular members. The proximal end of the second tubular member 120 may include a locking mechanism 190 that rotatably locks the second tubular member 120 to the first tubular member 110. When the locking mechanism is not engaged, the first and second tubular members are rotationally uncoupled, which allows the first tubular member 110, which is internal to the second tubular member 120, to rotate freely within the second tubular member 120.

Figure 3:
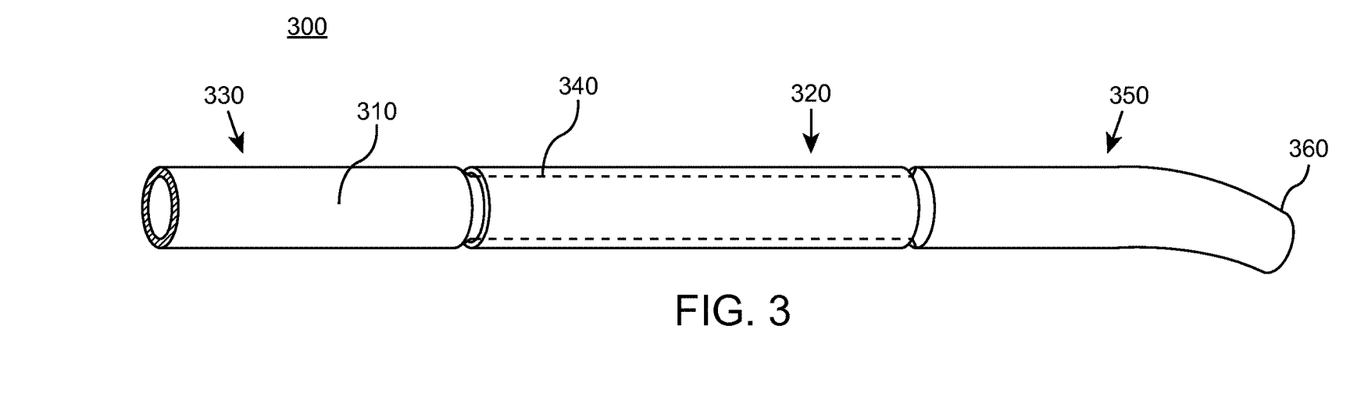
FIG. 3 shows a schematic side view of a catheter, according to embodiments of the present disclosure.

FIG. 3 shows a schematic side view of a catheter 300. The catheter 300 includes a first tubular member 310 that has a proximal portion 330, a central portion 340, and a distal portion 350. The catheter also includes a second tubular member 320 that surrounds the central portion 340 of the first tubular member 310. The catheter 300 also includes a distal tip 360 at the end of the distal portion 350 of the first tubular member.

Figure 4:
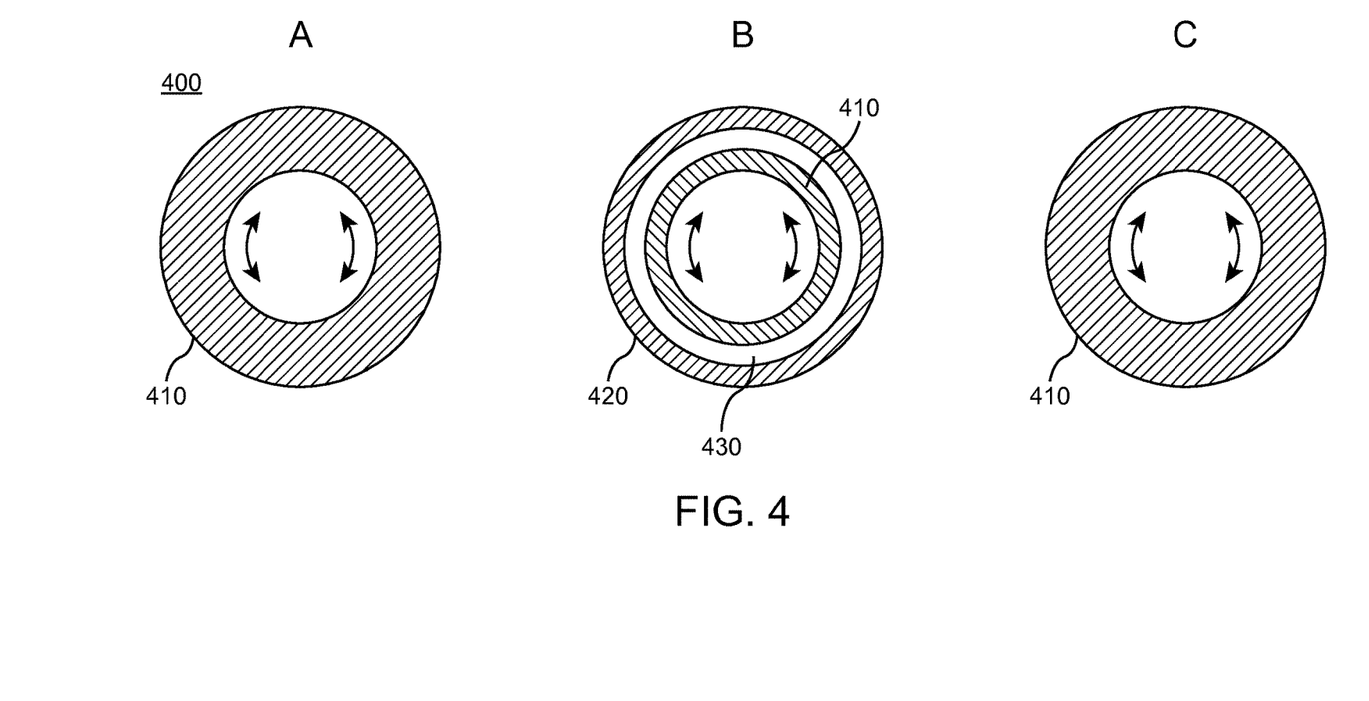
FIG. 4 shows cross-sectional views of the proximal (FIG. 4A), central (FIG. 4B), and distal (FIG. 4C) portions of a catheter, according to embodiments of the present disclosure.

FIG. 4 shows cross-sectional views of the proximal, central, and distal portions of a catheter 400. FIG. 4A shows a cross-sectional view of the proximal portion of the first tubular member 410 of the catheter 400. FIG. 4C shows a cross-sectional view of the distal portion of the first tubular member 410 of the catheter 400. The outside diameters of the proximal and distal portions of the catheter 400 may be substantially the same. FIG. 4B shows a cross-sectional view of the central portion of the catheter 400. As shown in FIG. 4B, the central portion includes a first tubular member 410 within a second tubular member 420. The outside diameter of the central portion of the first tubular member 410 is less than the outside diameters of the proximal and distal portions of the first tubular member, such that the outside diameter of the second tubular member 420 is substantially the same as the outside diameters of the proximal and distal portions of the first tubular member. A gap 430 may be present between the first and second tubular members in the central portion of the catheter. In some cases, the external surface of the central portion of the first tubular member and the internal surface of the second tubular member are closely aligned against each other (and may contact each other), but with enough space (or with a substantially low frictional resistance) such that the first and second tubular members can rotate independently of each other. In some instances, independent rotatability may be facilitated by the presence of a lubricant on either one or both of the facing surfaces of the central portion of the first tubular member and the second tubular member. Rotation of the first tubular member and the second tubular member are indicated by the rotational arrows in FIG. 4.

Methods

Aspects of the present disclosure include a method of performing a catheterization with a catheter as described herein. In certain embodiments, the method includes inserting the distal end of a catheter as described herein into a blood vessel (e.g., artery or vein), a body cavity (e.g., abdominal, thoracic, pelvic, pericardial space, etc.), or a hollow viscus (e.g., bladder, stomach, intestines, etc.) of a subject. The method may further include advancing the distal end of the catheter through the blood vessel, body cavity or hollow viscus, and transiently occupying a tortuous and/or spasmodic region of the blood vessel, body cavity or hollow viscus with at least a portion of the second tubular member of the catheter. In certain instances, the method further includes rotating the proximal end of the first tubular member within the second tubular member.

Particular embodiments of the catheterization methods are described in more detail below as they relate to an endovascular catheterization, however those of skill in the art will readily appreciate that the methods described herein may also be used for catheterization of other sites, such as a body cavity or hollow viscus of a subject as indicated above.

Embodiments of the present disclosure include a method of performing an endovascular catheterization with an endovascular catheter as described herein. In certain embodiments, the method includes inserting the distal end of a catheter as described herein into an artery. The method may further include advancing the distal end of the catheter through the artery, and transiently occupying a tortuous and/or spasmodic region of the artery with at least a portion of the second tubular member of the catheter. In certain instances, the method further includes rotating the proximal end of the first tubular member within the second tubular member.

The transient occupation of the tortuous region of the artery may apply frictional and/or topological constraints to the catheter that may impede or resist the rotation of the second tubular member. In some instances, resisting the rotation of the second tubular member may be sufficient to substantially prevent rotation of the second tubular member. In certain embodiments, the second tubular member is rotationally uncoupled from the first tubular member, and thus is not rotationally drivable by the operator. As such in these embodiments, the first and second tubular members are substantially freely rotatable with respect to each other. Thus, in certain cases, the first tubular member may be rotated within the second tubular member while the rotation of the second tubular member is impeded or resisted by frictional and/or topological constraints in the artery during use.

Embodiments of the present disclosure also include a method of accessing a patient's heart with an endovascular catheter. Embodiments of the method may include an endovascular catheter as summarized above.

Accordingly, some embodiments of the method include accessing a patient's heart with an endovascular catheter that includes a first tubular member and a second tubular member, as described herein. The method may further include inserting the distal end of the catheter into an artery that provides a route to the heart and advancing the distal end of the catheter through the artery toward the heart. While advancing, the second tubular member or a portion thereof may transiently occupy a tortuous and/or spasmodic region of the artery. The method may further include rotating the proximal portion of the first tubular member while the second tubular member is rotationally uncoupled from the first tubular member. In certain instances, as described above, this may facilitate rotation of the first tubular member within the second tubular member while allowing the second tubular member to remain rotationally still.

In certain embodiments, rotating the first tubular member may facilitate navigation or the advancement of the catheter through the tortuous and/or spasmodic region of the artery. In some instances, rotation of the first tubular member may include navigating (e.g., steering) the distal end of the catheter through the artery, such as from an aorta toward a targeted site (e.g., a targeted coronary artery, such as, by way of example, the right coronary artery or the left coronary artery). Embodiments of the method may further include advancing the distal end of the catheter into the targeted site (e.g., the targeted coronary artery).

In some embodiments of the method, allowing the second tubular member to remain rotationally uncoupled from the first tubular member may facilitate a reduction in the accumulation of torque in the catheter that would otherwise occur when the operator rotates the catheter while at least a portion of the second tubular member is transiently occupying a tortuous and/or spasmodic region of the artery. In some cases, a reduction in the accumulation of torque in the catheter may facilitate a reduction in the risk of the release of such torque that may result in a rapid unwinding of torque, a "helicoptering" or "whipping" event in which the distal portion of the catheter rotates suddenly as torque force overcomes the frictional (anti-rotational) restraining force. In some cases, a reduction in the risk of the release of such torque may reduce the risk of physical damage to the artery from the catheter.

Some embodiments of the method include rotationally connecting (and disconnecting) the first and second tubular members. When the first and second members are rotationally connected (e.g., rotationally coupled), rotation of the proximal end of the first tubular member drives rotation of the second tubular member. When an embodiment of the catheter includes a locking connector as summarized above, the method may include locking the locking connector to provide the first and second tubular members in a fixed rotational relationship. For instance, the locking connector may be locked at any point before, during or after the time the second tubular portion is transiently occupying the tortuous and/or spasmodic region of the artery. In certain embodiments, the method also includes unlocking the locking connector to rotationally uncouple the first and second tubular members, and thus allow the first tubular member to rotate within the second tubular member. As indicated above, the locking connector may be unlocked at any point before, during or after the time the second tubular portion is transiently occupying the tortuous and/or spasmodic region of the artery.

Some embodiments of a method are directed more broadly toward use of embodiments of the catheter throughout the vasculature, including veins as well as arteries, and toward diagnostic or interventional uses at non-cardiac sites. In these embodiments, the method is directed toward accessing a targeted site in a patient's vasculature with a catheter as summarized above. The method may include inserting the distal portion of the catheter into a blood vessel that provides a route to a targeted vascular site, and advancing the catheter through the blood vessel toward the targeted vascular site. In some embodiments, the method may include transiently occupying a tortuous and/or spasmodic region of the blood vessel with the second tubular member of the catheter. In these embodiments, the method may include rotating the proximal portion of the catheter so as to rotate the distal portion of the catheter while the first and second tubular members are rotationally uncoupled. For example, the first tubular member may be rotated within the second tubular member while allowing the second tubular member to remain rotationally still.

In some embodiments, a method of accessing a targeted vascular site with an endovascular catheter, as summarized above, may be performed for a diagnostic or treatment purpose. In these embodiments, the method includes inserting the distal portion of the catheter into a blood vessel that provides a route to the targeted vascular site, and then advancing the catheter through the blood vessel toward the targeted site. In some instances, the catheter (e.g., the second tubular member of the catheter) may become rotationally entrapped within a tortuous and/or spasmodic region of the vessel. In these embodiments, the method may include driving the rotation of the first tubular member of the catheter within the second tubular member.

An example of an embodiment of the method is described below. In some embodiments, the method includes inserting the distal end of the catheter into a site of entry for a vascular route to a target vascular site. The method may further include advancing the distal end (and the catheter length) upstream, e.g., over a guidewire, through the vascular route toward the target site. The method may further include advancing the distal end of the catheter into a tortuous and/or spasmodic region of the vascular route. The method may further include rotating the distal end of the catheter to facilitate navigating or steering the catheter through the tortuous and/or spasmodic region. The method may further include transiently occupying the tortuous and/or spasmodic region with at least a part of the central portion of the catheter. The method may further include rotating the distal end of the catheter to facilitate navigating or steering the distal end toward the target site, as for example, the left coronary artery or the right coronary artery, while second tubular member is rotationally uncoupled from the central portion of the first tubular member of the catheter. The method may further include advancing the distal end of the catheter to the target site, for example, the left or right coronary artery.

Figure 2:
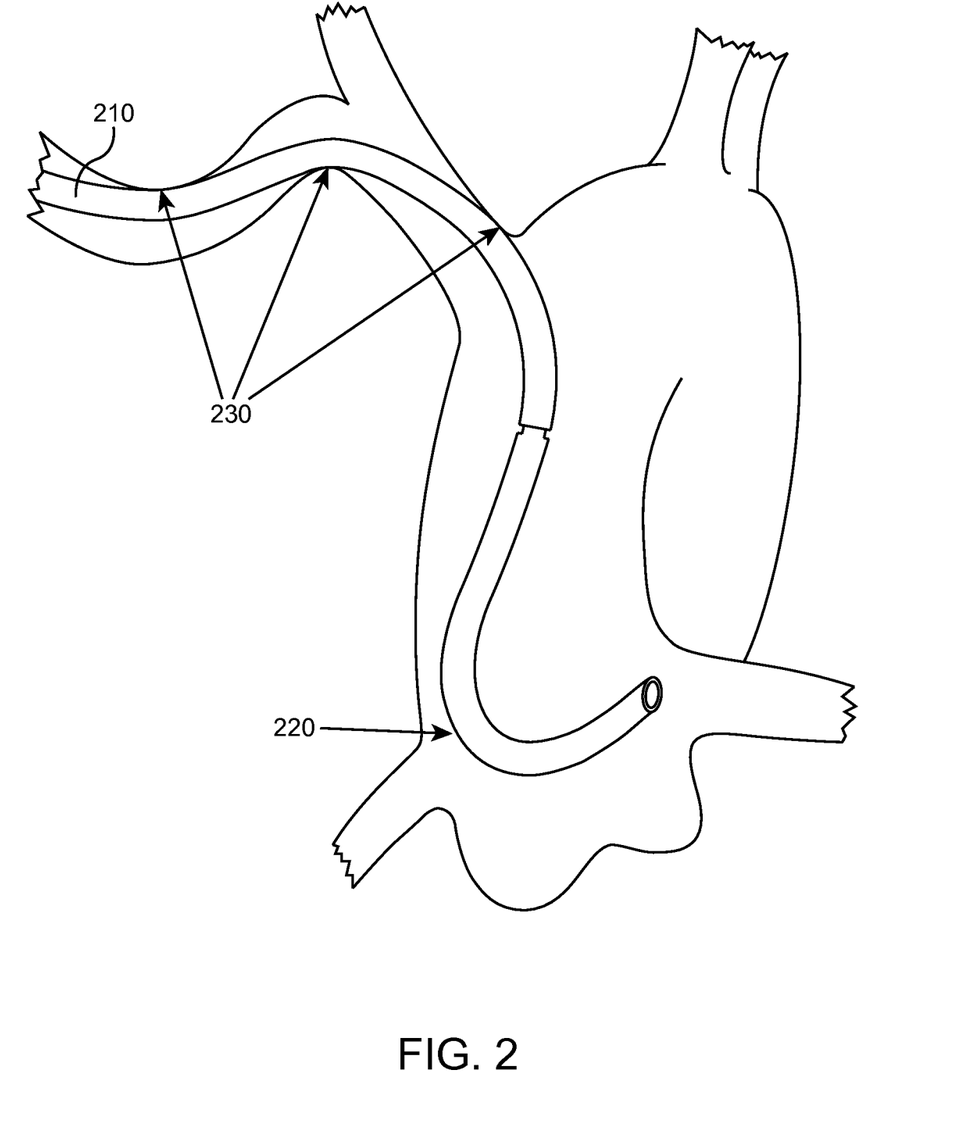
FIG. 2 shows a view of an embodiment of a catheter as it is being navigated through tortuous and/or spasmodic regions of vasculature en route to the heart, according to embodiments of the present disclosure.

FIG. 2 shows a view of an embodiment of a catheter as it is being navigated through tortuous (and/or spasmodic) regions of vasculature en route to the heart. In this example of a method, an embodiment of the catheter is being used for trans-radial coronary angiography. There may be several points in the tortuous subclavian artery where friction is applied to the external surface of the catheter (see arrows indicated by 230), either due to the tortuosity of the artery and/or arterial spasm. The distal end 220 of the catheter may be a flexible pre-shaped form or native form (when the distal portion is released from a linear constraint) that suits the specifics of the procedure. The rotational force applied at the proximal end of the catheter is transmitted to the distal end through the rotation of the first tubular member. The first tubular member substantially freely rotates within the second tubular member 210 despite the frictional forces and/or topological constraints being applied on the second tubular member, which may impede or restrict the rotation of the second tubular member. As summarized above, embodiments of the catheter may include a locking mechanism, which, when engaged, configures the catheter such that the first and second tubular members are in a fixed rotational relationship. For example, when the locking mechanism is engaged, rotation of the proximal end of the catheter manifests as rotation of the catheter as a whole. When the locking mechanism is disengaged, the first and second tubular members are rotationally uncoupled as described above.

In practice, embodiments of the method may include initiating a catheterization procedure with the first and second tubular members locked. In this case, the method may include unlocking the first and second tubular members prior to rotating the distal end of the catheter to facilitate navigating or steering the distal end toward the target site while the central portion of the catheter is transiently occupying the tortuous and/or spasmodic region of the vascular route.

Utility

The subject devices and methods find use in a variety of different applications where catheterization (e.g., endovascular catheterization) is desired. As described herein, catheters of the present disclosure may be described, for example, in relation to a catheterization procedure, such as an endovascular catheterization using a catheter configured for an endovascular catheterization. These descriptions herein are examples of embodiments of the present disclosure, and the full scope of embodiments of the present disclosure includes catheters and catheterization methods that find use in the catheterization of a blood vessel (e.g., artery or vein), a body cavity (e.g., abdominal, thoracic, pelvic, pericardial space, etc.), and a hollow viscus (e.g., bladder, stomach, intestines, etc.), and the like, of a subject.

As described above, rotation of the catheter, as controlled by torque applied at the proximal end of the catheter by an operator, such as an interventional cardiologist, can facilitate navigation of the catheter through various tortuous and/or spasmodic arterial regions. In addition, in some embodiments, rotation of the catheter, and consequent rotation of the distal end of the catheter (e.g., a curved distal tip), may facilitate directing the distal end toward the entry into a targeted vessel, such as a coronary artery during a cardiac catheterization procedure.

Catheter rotation within an artery, however, can be constrained by friction between the catheter and arterial walls, such as through tortuous and/or spasmodic regions of the artery. The subject devices and methods also find use in the prevention or reduction in the risk of occurrence of undesired side effects associated with endovascular catheterization. For example, in some instances, rotating a first tubular member within a second tubular member as described herein while the second tubular member is in a tortuous and/or spasmodic arterial region may facilitate a reduction in patient discomfort and may shorten the length of time needed to perform the procedure. In certain embodiments, rotation of the catheter as described herein may facilitate a reduction in constriction of the artery, thereby facilitating passage of the catheter through the artery. In some instances, rotation of the catheter as described herein while the second tubular member is in a tortuous and/or spasmodic region can facilitate a reduction in the kinking of the catheter, which may facilitate the operator's ability to steer the catheter by rotation.

The radial artery approach to the heart has clinical advantages over the femoral route, including fewer access site complications, and less bleeding from the entry site. These advantages can be particularly significant in heart attack patients who may be receiving multiple anticoagulants coincident with the catheterization. However, the radial artery approach can have a degree of tortuosity that is greater than the femoral route, and this consideration can pose a barrier, in practice, for the use of this route in spite of its general advantages with regard to safety and outcome. In addition, the radial artery has a tendency to spasm. The tortuosity and spasm encountered during trans-radial catheterization produce friction on the outside of the catheter and may limit the operator's ability to rotate the catheter within the body. As such, embodiments of the catheters of the present disclosure may facilitate trans-radial catheterization. In certain embodiments, rotation of the catheter as described herein may facilitate a catheterization in a tortuous and/or spasmodic radial artery, thereby facilitating passage of the catheter through the artery.

Kits

Also provided are kits that find use in practicing the subject methods, as described above. For example, kits for practicing the subject methods may include a sterile packaging containing a catheter as described herein. For example, in certain embodiments, the kits include a sealed package configured to maintain the sterility of the catheter. The sealed package may be sealed such that substantially no external contaminants, such as dirt, microbes (e.g., fungi, bacteria, viruses, spore forms, etc.), liquids, gases, and the like, are able to enter the sealed package. For example, the sealed package may be sealed such the package is watertight and/or air-tight.

In certain embodiments, the kit may further include one or more additional items that may find use in a catheterization procedure. For instance, the kit may include additional items, such as, but not limited to, a sterile wipe, an antiseptic solution, a local anesthetic, and the like. The additional items may be provided in one or more separate containers, which may each include a different component of the kit. The one or more containers may be provided as separate individual containers, or may be connected or formed together as a single unit. For example, the container for an antiseptic solution or a local anesthetic may be a vial, a bottle, and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-ray, computer-readable memory, etc., on which the information has been recorded or stored. Yet another means that may be present is a website address which may be used via the Internet to access the information at a removed site. Any convenient means may be present in the kits.

The preceding merely illustrates the principles of the disclosure. All statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, e.g., any elements developed that perform the same function, regardless of structure. The scope of the present disclosure, therefore, is not intended to be limited to the exemplary embodiments shown and described herein. Rather, the scope and spirit of present disclosure is embodied by the appended claims.

That which is claimed is:

1. A catheter comprising:
    a first tubular member comprising a proximal portion having a proximal end, a central portion, a distal portion having a distal end, a lumen that extends from the proximal end to the distal end, and a longitudinal axis;
    a second tubular member surrounding at least a portion of the central portion of the first tubular member, the second tubular member having a proximal end, a distal end, and a longitudinal axis;
    a locking connector positioned at a junction between the proximal end of the second tubular member and the proximal portion of the first tubular member; and
    an external surface comprising an external surface of the proximal portion and the distal portion of the first tubular member, and an external surface of the second tubular member,
    wherein the locking connector has a locked state and an unlocked state,
    wherein when the locking connector is in the unlocked state the second tubular member is configured to freely rotate about the central portion of the first tubular member, and
    wherein the first tubular member and the second tubular member are dimensioned such that the second tubular member does not significantly slide over the first tubular member in either a proximal or distal direction when the locking connector is in the locked state or the unlocked state.

2. The catheter of claim 1, wherein the distal portion of the first tubular member extends distally beyond the distal end of the second tubular member.

3. The catheter of claim 1, wherein the catheter is an endovascular catheter sized for an endovascular catheterization procedure.

4. A method of performing a catheterization, the method comprising:
    inserting the distal end of a catheter according to claim 3 into a blood vessel, a body cavity or a hollow viscus of a subject;
    advancing the distal end of the catheter through the blood vessel, the body cavity or the hollow viscus;
    transiently occupying a tortuous and/or a spasmodic region of the blood vessel, the body cavity or the hollow viscus with at least a portion of the second tubular member of the catheter; and
    rotating the proximal end of the first tubular member within the second tubular member when the locking connector is in the unlocked state.

5. The method of claim 4, wherein transiently occupying the tortuous and/or the spasmodic region of the blood vessel, the body cavity or the hollow viscus applies frictional and/or topological constraints substantially preventing rotation of the second tubular member.

6. The method of claim 4, wherein the blood vessel comprises a radial artery, a brachial artery, or a femoral artery.

7. The method of claim 4, wherein rotating the first tubular member further comprises advancing the catheter through the tortuous and/or the spasmodic region.

8. The method of claim 4, wherein the method further comprises:
    locking the locking connector to provide the first tubular member and the second tubular member in a fixed rotational relationship; and
    unlocking the locking connector to allow the first tubular member to rotate within the second tubular member.

9. The catheter of claim 1, wherein the catheter is configured for catheterization of a body cavity or a hollow viscus of a subject.

10. The catheter of claim 1, wherein when the locking connector is in the unlocked state the first tubular member is configured to be rotatably drivable from the proximal end of the first tubular member and the second tubular member is rotationally uncoupled from the first tubular member.

11. The catheter of claim 10, wherein the proximal end of the first tubular member comprises one or more laterally extending tabs.

12. The catheter of claim 10, wherein when the locking connector is in the unlocked state the first tubular member is configured to rotate within the second tubular member while the second tubular member remains rotationally still.

13. The catheter of claim 12, further comprising one or more tabs extending laterally from the proximal end of the first tubular member and configured to rotate the first tubular member within the second tubular member.

14. The catheter of claim 1, wherein the proximal portion and the distal portion of the first tubular member have an outside diameter substantially the same as an outside diameter of the second tubular member.

15. The catheter of claim 1, wherein the central portion of the first tubular member has an outside diameter less than the outside diameter of the proximal portion and the distal portion of the first tubular member.

16. The catheter of claim 1, wherein the central portion of the first tubular member comprises an external surface and the second tubular member comprises a lumen having an internal surface, and wherein the catheter further comprises a lubricant between the external surface of the central portion of the first tubular member and the internal surface of the second tubular member.

17. The catheter of claim 16, wherein when the locking connector is in the unlocked state the external surface of the central portion of the first tubular member and the internal surface of the second tubular member are closely aligned against each other with a gap such that the first tubular member and the second tubular member can rotate independently of each other.

18. The catheter of claim 1, wherein the locking connector is in the locked state and is configured to engage the first tubular member and the second tubular member into a fixed rotational relationship.

19. The catheter of claim 1, wherein the locking connector is annular and comprises an internal threading complimentary to a threading disposed circumferentially on an external surface of the first tubular member.

20. The catheter of claim 1, wherein when the locking connector is in the unlocked state the external surface of the second tubular member is rotatably independent with respect to the proximal portion and the distal portion of the first tubular member.

21. The catheter of claim 20, wherein rotatability is facilitated by a lubricant on either one or both of facing surfaces of the central portion of the first tubular member and the second tubular member.

22. The catheter of claim 1, wherein the locking connector is fixed externally to the second tubular member at the proximal end of the second tubular member.

23. The catheter of claim 1, wherein the locking connector is fixed to the proximal end of the second tubular member.

24. A catheterization kit comprising:
   a sterile packaging containing:
      a catheter comprising:
         a first tubular member comprising a proximal portion having a proximal end, a central portion, a distal portion having a distal end, a lumen that extends from the proximal end to the distal end, and a longitudinal axis;
         a second tubular member surrounding at least a portion of the central portion of the first tubular member, the second tubular member having a proximal end, a distal end, and a longitudinal axis;
         a locking connector positioned at a junction between the proximal end of the second tubular member and the proximal portion of the first tubular member; and
         an external surface comprising an external surface of the proximal portion and the distal portion of the first tubular member, and an external surface of the second tubular member,
      wherein the locking connector has a locked state and an unlocked state,
      wherein when the locking connector is in the unlocked state the second tubular member is configured to freely rotate about the central portion of the first tubular member, and
      wherein the first tubular member and the second tubular member are dimensioned such that the second tubular member does not significantly slide over the first tubular member in either a proximal or distal direction when the locking connector is in the locked state or the unlocked state.

* * * * *